(12) United States Patent
Rizzuto et al.

(10) Patent No.: US 9,655,638 B2
(45) Date of Patent: May 23, 2017

(54) TWIN FORCEPS FOR SINGLE ACCESS LAPAROSCOPY

(71) Applicants: Antonia Rizzuto, Rende (IT); Guido Danieli, Rende (IT); Paola Nudo, Rende (IT); Mario Donnici, Rende (IT); Pasquale Francesco Greco, Rende (IT); Rosario Sacco, Rende (IT)

(72) Inventors: Antonia Rizzuto, Rende (IT); Guido Danieli, Rende (IT); Paola Nudo, Rende (IT); Mario Donnici, Rende (IT); Pasquale Francesco Greco, Rende (IT); Rosario Sacco, Rende (IT)

(73) Assignee: Calabrian High Tech SRL, Rende (IT)

( * ) Notice: Subject to any disclaimer, the term of this patent is extended or adjusted under 35 U.S.C. 154(b) by 0 days.

(21) Appl. No.: 14/376,420

(22) PCT Filed: Feb. 19, 2013

(86) PCT No.: PCT/IT2013/000052
§ 371 (c)(1),
(2) Date: Aug. 2, 2014

(87) PCT Pub. No.: WO2013/140426
PCT Pub. Date: Sep. 26, 2013

(65) Prior Publication Data
US 2014/0378998 A1     Dec. 25, 2014

(30) Foreign Application Priority Data

Feb. 21, 2012 (IT) .............................. CS2012A0006
Sep. 7, 2012 (IT) .............................. CS2012A0032
Jan. 11, 2013 (IT) .............................. CS2013A0001

(51) Int. Cl.
A61B 17/00    (2006.01)
A61B 17/29    (2006.01)
A61B 34/30    (2016.01)

(52) U.S. Cl.
CPC .......... *A61B 17/2909* (2013.01); *A61B 17/29* (2013.01); *A61B 2017/00353* (2013.01);
(Continued)

(58) Field of Classification Search
CPC . A61B 17/29; A61B 17/2909; A61B 19/2203; A61B 2017/00353;
(Continued)

(56) References Cited

U.S. PATENT DOCUMENTS 5,511,564 A    4/1996   Wilk
5,683,349 A    11/1997  Makower et al.
(Continued)

FOREIGN PATENT DOCUMENTS

EP    2 158 836 A2       3/2010
WO    WO 94/18893 A1     9/1994
WO    WO 2009/157719 A2  12/2009

OTHER PUBLICATIONS

Search Report of foreign priority CS2013A000001 of the instant application, Oct. 19, 2012, from Italian Ministry of Economic Development.

(Continued)

*Primary Examiner* — Ashley Fishback
(74) *Attorney, Agent, or Firm* — Cahn & Samuels, LLP (57) ABSTRACT

The patent is relative to a new instrument for single access laparoscopy that tries to overcome the limits of the present instrumentation used in this technique, that usually allows to use only one forceps, which does not allow to keep the tissues tenses to work with the surgical instrument. To (Continued)

overcome this limitation, the proposed instrument presents two arms, arranged in parallel presenting a diameter equal to half of the main body in the opening direction of the same, while in the direction perpendicular to this these arms can have an higher diameter, provided its shape be entirely circumscribed by the external dimension of the initial body, and each bearing at the tip a forceps, which may be mounted directly on the arms or on two auxiliary arms. The internal mechanism allows opening the two arms, not necessarily in the plane of rotation of the control rings, while the forceps bend toward the inside, keeping their configuration, being all this controlled by a single command. Two additional commands allow then to open and close the forceps individually, and each command can be locked in any position. The forceps can be opened in any direction relative to the plane of the arms, which can also be adjustable in a particular version, as well as it is possible that one or both of the forceps are replaced by a tool of a different type. The instrument can also be made with curvature of the body opposite to that of the arms, the latter being also controlled with a further command. Finally, there are versions of different pliers with robotic motion control and implementation.

3 Claims, 6 Drawing Sheets

(52) U.S. Cl.
CPC ............... *A61B 2017/00398* (2013.01); *A61B 2017/00464* (2013.01); *A61B 2017/00539* (2013.01); *A61B 2017/00544* (2013.01); *A61B 2017/291* (2013.01); *A61B 2017/2904* (2013.01); *A61B 2017/2906* (2013.01); *A61B 2017/2908* (2013.01); *A61B 2017/2923* (2013.01); *A61B 2017/2931* (2013.01); *A61B 2017/2943* (2013.01); *A61B 2017/2945* (2013.01); *A61B 2017/2946* (2013.01); *A61B 2034/302* (2016.02)

(58) Field of Classification Search
CPC .... A61B 2017/00398; A61B 2034/302; A61B 2017/2906
See application file for complete search history.

(56) References Cited

U.S. PATENT DOCUMENTS

| | | | |
|---|---|---|---|
| 5,997,565 A | 12/1999 | Inoue | |
| 6,214,028 B1 | 4/2001 | Yoon et al. | |
| 6,423,054 B1 | 7/2002 | Ouchi | |
| 7,867,228 B2 * | 1/2011 | Nobis | A61B 17/320016 606/45 |
| 2003/0114839 A1 | 6/2003 | Looper et al. | |
| 2004/0138525 A1 | 7/2004 | Saadat et al. | |
| 2005/0234296 A1 | 10/2005 | Saadat et al. | |
| 2006/0100644 A1 | 5/2006 | Viola | |
| 2007/0179340 A1* | 8/2007 | Jorgensen | A61B 1/04 600/139 |
| 2007/0299387 A1 | 12/2007 | Williams et al. | |
| 2010/0198253 A1 | 8/2010 | Jinno | |
| 2011/0106145 A1 | 5/2011 | Jeong | |
| 2011/0230723 A1 | 9/2011 | Castro et al. | |
| 2013/0165907 A1 | 6/2013 | Attar et al. | |

OTHER PUBLICATIONS

Search Report of foreign priority CS2013A000001 of the instant application, Sep. 9, 2013, from Italian Ministry of Economic Development.
Search Report of foreign priority CS2013A000021 of the instant application, May 7, 2014, from Italian Ministry of Economic Development.
International Search Report, Jun. 12, 2013, from International Phase of the instant application.

* cited by examiner

TWIN FORCEPS FOR SINGLE ACCESS LAPAROSCOPY

STATE OF THE ART

Recent years have seen the emergence of new methods in the field of minimally invasive surgery, among them the scientific evidence has imposed on the European scene SAL (Single Access Laparoscopy).

The method is based on the ability to play the conventional laparoscopic techniques through a single access route to the abdominal wall. There are many advantages to this method, in strictly clinical (decreased postoperative pain, risk of incisional hernia associated with the use of multiple trocar, no visible scar) and in terms of costs (reduction in hospital stay).

Limit of the method: the technical difficulties in some anatomical regions (the pelvic cavity and the hepatic bed) due to lack of appropriate equipment.

The abdominal access of a width not greater than 2 cm does not allow in fact, through the kits available on the market, the positioning of a number exceeding three tools, including the optic. In some cases this leads to an incorrect visualization of anatomical structures due to lack of tissue distension characteristic of conventional laparoscopy. In the latter the tension of the tissue during dissection is ensured by two grasping forceps, which, in the SAL is not possible to have. Solutions such as the one represented by patent application DE102009001278 (A1)—"Medical instrument, for surgery with minimal invasion or endoscopy, has a swing shaft or instrument housing at the distal end of a shaft in a two-part structure" or of patent application EP2377477A1 "Surgical Instrument Having Movable Head Instrument" in fact not solve the problem, because although adjusFigure, do not allow two forceps, clamps or if you prefer, separated, but always and only one. As for the solution proposed by M. Williams S. et al. in the document US2007/0299387, it is a complex instrumentation adapted to guide other flexible instruments within the appropriate channels, then is not possible to speak of a single instrument, even if such a term is used improperly, not to mention that precisely such a "tool" per se possesses neither forceps nor any other instrument to enter into direct contact with the tissue. As for the quotation of paragraphs 0034 and 0042 of the same document, referred to in the research report, one can observe that the numbers 12 and 14 refer not to the diameter, but to the numbers used in the figures to indicate precisely the tubes used to pass the real surgical instruments, which already existed.

Purpose of the present invention, which refers to the Italian patent applications CS2012A000006, CS2012A000032 and CS2013A000001, is to remedy this situation, through the proposal of an innovative instrument for surgical laparoscopy, which could be introduced by a single hole 12 to 15 mm in diameter as if it were a single instrument, but which present in the final part two arms of smaller diameter initially parallel (each with a maximum diameter half the diameter of the initial part in the direction of tiling, but possibly greater in the direction perpendicular to this, provided that the profile of the arm is limited to that of the initial part), and which can then be separated into two branches, each of which is equipped with a forceps for grasping tissue, and which is possibly also able to stretch the tissue once grasped in two points. Moreover, these arms may also be curved or even flexible.

DESCRIPTION OF THE PREFERRED EMBODIMENT

In particular the new instrument for laparoscopy mono-access will have circular cross-section in the initial part of diameter 12 to 15 mm, and then end with two arms each of diameter half of the initial at the end of each of which is present a clamp-forceps able to grab the tissues. However, in order to simplify the surgery, it would be useful to have a single opening command, but also to provide simultaneous tilting towards the inside of the forceps, in order to facilitate the gripping capacity.

Figure 1:
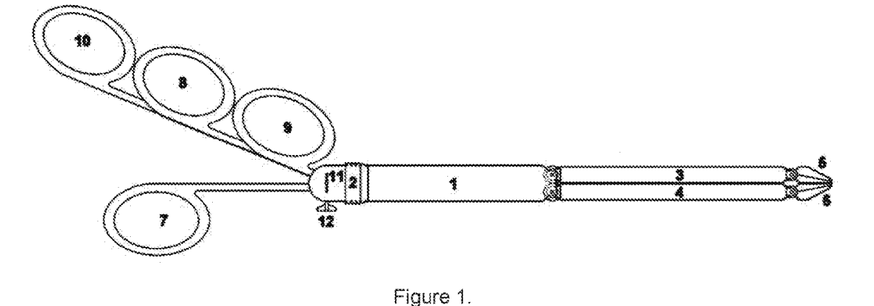

FIG. 1 shows precisely the twin instrument that, starting from a single body of circular cross-section of 12 mm (1) (a standard introduction trocar (2) can be used, in which the instrument can slide varying its depth of penetration), is then divided into two arms (3 and 4), each with forceps at the ends (5 and 6). The initial part of the surgical instrument has four rings, one lower and fixed (7), the other three on the upper part (8, 9 and 10) for controlling the instrument in all its peculiarities.

On the exterior of the instrument three fins are present, two symmetrically placed (11), (in the view only one is visible) that serve to lock the position of the forceps, the third on the side of the fixed ring (12), serves to block the opening degree of the two arms. The three rings (8, 9 and 10) can be operated jointly by blocking the fins (11). This joint movement must cause the opening of the two arms (3 and 4) and the simultaneous counter-rotation of the forceps (5 and 6), which must still maintain their initial configuration, which are open or closed. In particular the three rings (8, 9 and 10) will have to be, the central one (8) dedicated to the separation and rapprochement of the two arms (3 and 4), while the side ones (9 and 10) are in charge of opening and closing the forceps, when operated in a different manner from the center ring.

Figure 2:
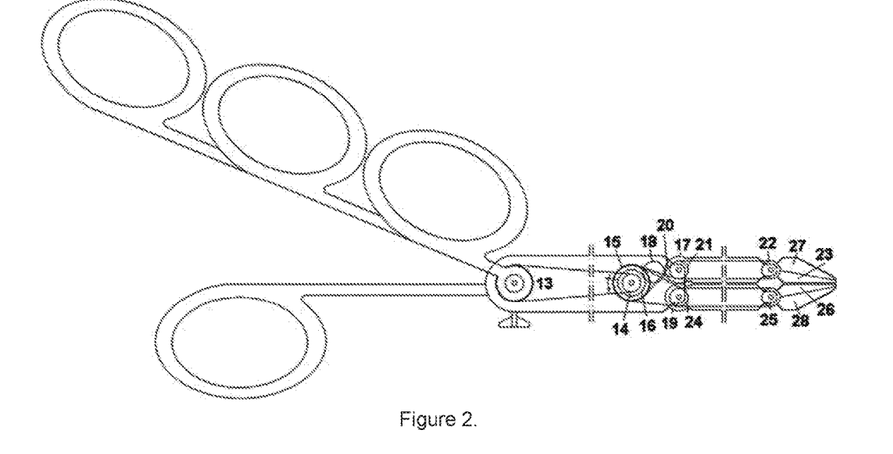

To understand how this can be realized, we must go to the FIG. 2, which shows a possible embodiment of the inner part of the instrument, which allows to understand how it works.

In particular, the FIG. 2 (in which the instrument has been shortened with the sections highlighted with dotted lines, in order to make the drawing more readable) shows the arrangement of internal cables and of the toothed wheels which control the handling of the instrument. In particular, note that the operating ring (8) is rigidly connected to a pulley (13) which controls, via transmission cables, the pulley (14), of smaller diameter to limit the excursion of the ring allowing a more wide relative rotation between the instruments. In particular in the drawing there is a 2:1 ratio between the radius of the wheel (13) and that of (14), for which a manual rotation of 22.5 degrees will correspond to a rotation of the wheel (14) of 45°. Fixes to this pulley there are both a pulley (15) of diameter equal to (13) and a gear (16) of which only the primitive is shown, which, meshing with gear (17) through an idle gear (18) opens in a direction arm (3) of FIG. 1, while arm (4) is opened in the opposite direction thanks to meshing of the gear (17) with (19). Note how the two gears (17 and 19) are fixed respectively to the arms (3 and 4). To obtain the opposite rotation of the two forceps, starting from the pulley (15), again via cable transmission but crossing the cables themselves (20), motion is transmitted to the pulley (21), coaxial with the wheel (17), but free to rotate relative to this, and presenting a diameter exactly half of that of the pulley (15). To this pulley is then connected a further pulley (22) which is connected to the part of the forceps (23) whose movement is controlled from the ring (8), which will rotate through an angle twice and in opposite direction of the gear (17) given the ratio between the diameters of the pulleys. In the case of the arm (4), coaxial with the wheel (19), there will be a further pulley (24), also free to rotate with respect to (19), and as before in diameter exactly half of that of the pulley (15), and connected by cable transmission with this but without reversal of movement. As in the previous case to this pulley is then connected a further pulley (25) which is connected to the part whose movement is controlled as before from the ring (8) of forceps (26), which rotates by an angle twice the wheel (19) because of the relationship between the diameters of the pulleys. Finally, as regards the movable parts of forceps operable independently by the rings (9) and (10), that is to say the members (27) and (28), their mechanism is similar to the one the described above, but without the gears, so that if the ring that controls (for example 9), hinged on the same axis of pulley (13), is moved along with this, for example fixing it through fin (11), the movement of the movable part (27) will be identical to that of the part whose movement is controlled from the ring (8). Conversely, blocked the central ring (8) with the fin (12), and releasing the fins (11), the movable parts of the forceps (27) and (28) can be operated independently for opening and closing through the rings (9) and (10) respectively.

Figure 3:
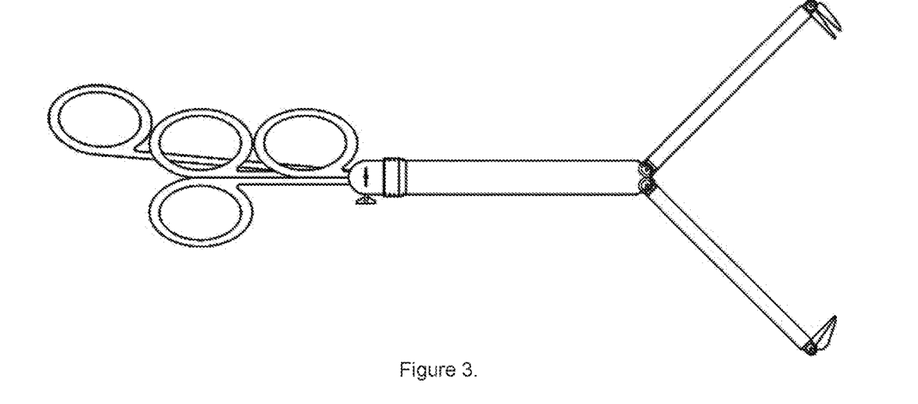

FIG. 3 shows the opening of the two instruments, the inclination of the forceps in the opposite direction, one of which is shown in the open position.

Figure 4:
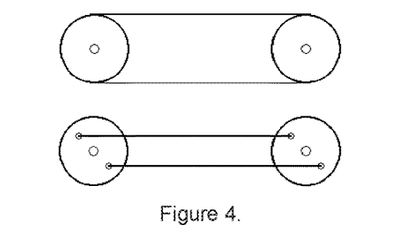
Figure 5:
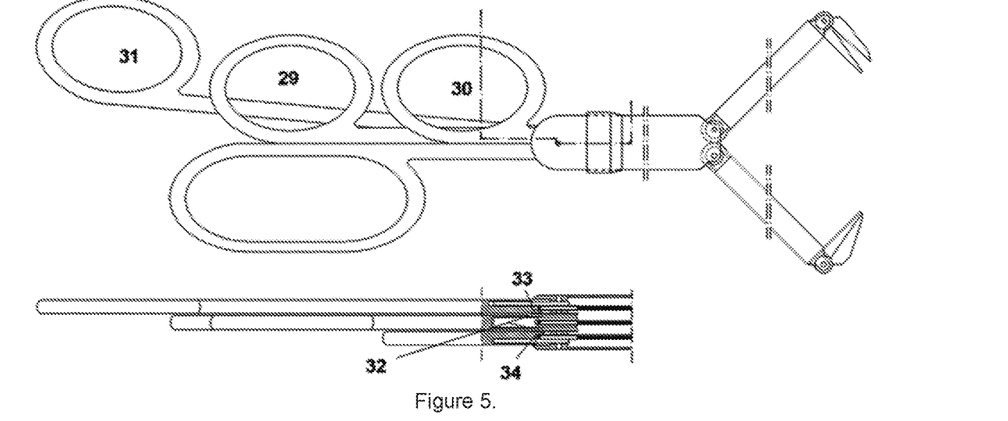

It should be noted that this system can be realized also with gears only or even only with transmission cables, or, as shown in FIG. 4, building a sort of articulated parallelogram, much safer and capable of transmitting higher stresses, if the rotations are maintained at below 180 degrees. Even the double rotation of the forceps with respect to the instrument can be canceled using pulleys of the same diameter, or even increased for example to a 1:3 ratio simply by altering the diameters of the pulleys, or adding further reduction pulleys in the transmission path. Other locking methods may be evaluated, for example by leaving a little more space between the three upper rings, so as to allow locking the corresponding ring moving it towards the fulcrum, and inserting a wedge between the central ring and the side ones, that move the movable parts of the forceps in the case of locking of forceps or a wedge between two fixed surfaces in the case of the central ring. This is illustrated in FIG. 5, in which are indicated with (29), (30) and (31) the three rings, showing below a section view from above in which it is noted that each of the rods controlled by the rings is composed of two elements free to slide on each other, with the external rods that have wedges that engage between the central ring and the ones commanding the two forceps, while the central rod can get stuck on the frame of the same instrument, so as to lock with respect to this. In particular in the drawing the rod (33) is free to move, the (32) is locked on the frame and the (34) to (32). Finally the instrument may be realized either as drawn, i.e. in such a way that it is closed (with the two parallel arms) with the rings far apart, or closed with the rings close together, opening rings and arms in one time: it is a simple reverse motion. In this case, however, it may be more practical to put the control ring of the opening closest to the instrument, and the other two farther out.

Figure 6:
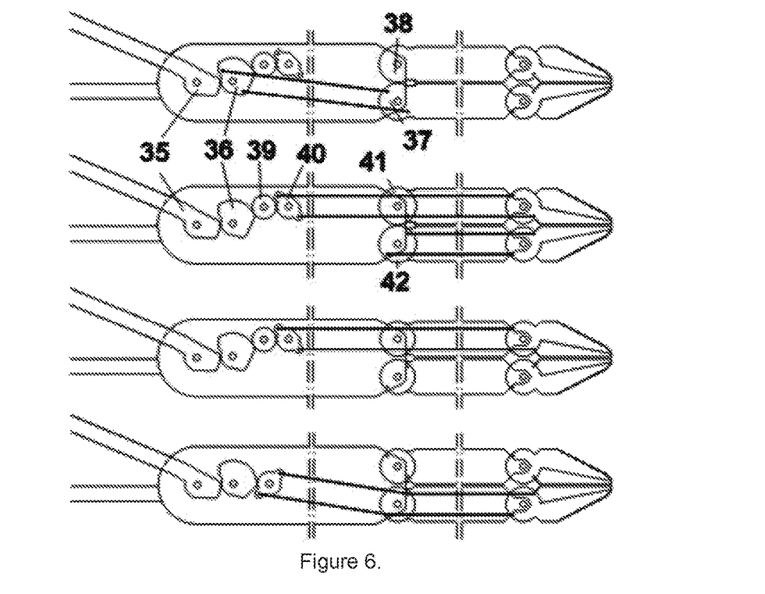
Figure 7:
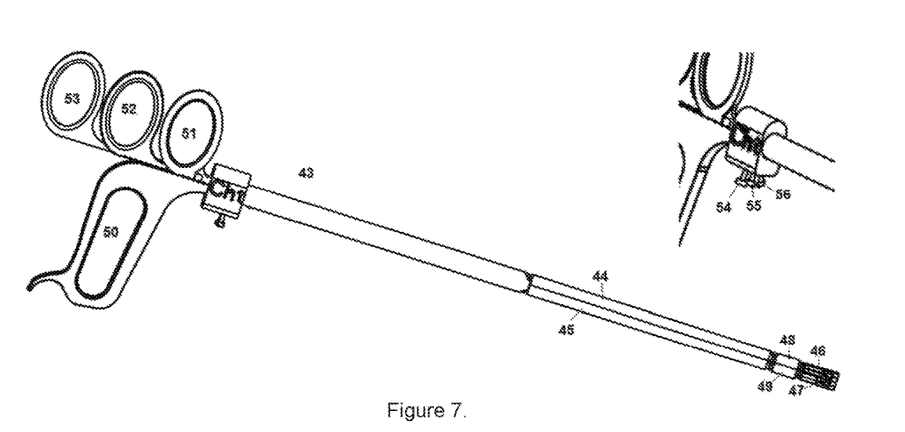

FIG. 6 shows four possible internal mechanisms using gears and four bar links in which, given the limited rotation required, use of gears is almost always made, having a radius on the one side, and a different one on the other, in order to reduce the space required. In particular the first of the four images shows the opening mechanism of the two arms, where (35) is the control rod which presents, on the side opposite to the ring, a toothed sector, which controls gear (36) having a smaller radius (half), and from which a four bar link takes origin, which moves the gear (37) which meshes with the (38) causing the symmetrical opening of the arms. In the second image, which always represents the main command, note that downstream of the same gear (36), there are a pair of gears (39 and 40) (being (39) idle) which in turn command via four bar link two further gears (41 and 42) which mesh with each other so as to reverse the motion, and are connected by four bar link to the fixed parts of forceps. The last two shows the mechanisms for opening the forceps with their internal connections. It should be noted that, as already said, the gears are here represented for simplicity as a simple friction wheels, and may be realized with any profile it is considered appropriate, though perhaps those that best fit might be the cycloidal profiles used in watches. Alternatively to what previously described, in which the opening command of the arms caused also the rotation in the opposite direction of the fixed part of the forceps, it is possible a second configuration in which such counter rotation acts on short secondary arms, at the end of which are placed the forceps opening symmetrically, which also has the advantage of allowing the opening the forceps in any direction with respect to the opening of the arms. FIG. 7 shows precisely the new twin instrument that, starting from a single body of circular cross-section of 12-15 mm (43) (for which a standard trocar can be used for introduction and in which it can slide by varying its depth of penetration), divide then in two arms (44 and 45), each bearing forceps (46 and 47) placed at the end of very short secondary arm (48, 49). As in the previous case, the initial part of the instrument operator has four rings, one lower and fixed (50), the other three upper (51, 52 and 53) for controlling the instrument in all its peculiarities.

On the exterior of the instrument are present then three locking actuators of the three command rings (54, 55 and 56). While in the case seen up to now to maintain the forceps in their opening or closing position was necessary to maneuver the three rings simultaneously, in this configuration it is no longer necessary. This happens because the command of opening and closing of the forceps is totally independent from that of divarication of the arms. Therefore, the physician can maneuver the opening and closing of the arms in a manner totally independent of the position of the forceps.

Figure 8:
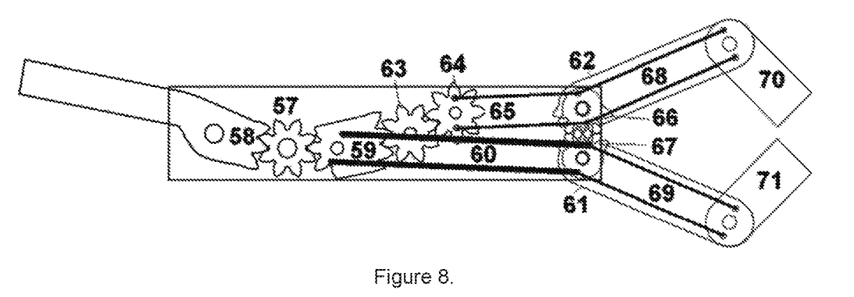
Figure 9:
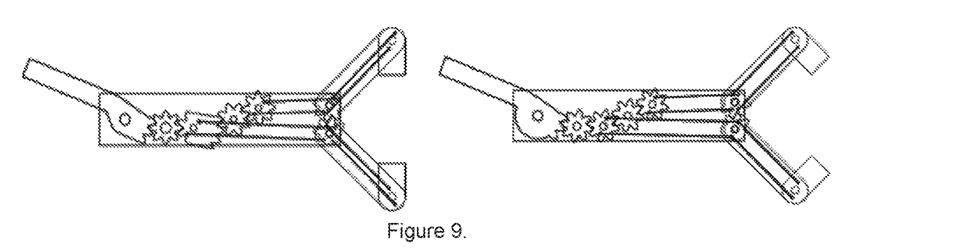

In particular the mechanism for opening and closing of the arms will be controlled by one of the three rings, or by suitable mechanisms connected to a robot (the central ring in the preferred embodiment, but only to help the physician to remember which is the one that takes care of this task) with a mechanism similar to that of the previous patent, which is illustrated in FIG. 8 (in which the instrument has been shortened so that the drawing is more readable) only as a possible example of embodiment. It is known that in this case, contrary to what previously illustrated, is preferred that the arms closed position matches the position rings close together, and not as previously illustrated, and how this has been obtained by simply interposing a gear (57) (involute profile teeth with thrust angle 35°) between the control rod (58) and the real author of the command (59), connected via a four bar link (60) to the frame of the lower arm (61, in red), which in turn meshes with the upper arm (62) so that the two rotate in opposite direction. Note also how it is preferred to use systems of gears and four bar links, in place of a control cables in order to ensure greater safety of implementation, without however that such an embodiment should be qualifying for the patent itself. It is also known as the pitch circle radius of the toothing placed on the control rod (58) is double of both gear (57) and the gear (59) driving arms opening, which presents, however, again double pitch radius on the opposite side where is commands, through the gears (63) and (64) and the four bar link (65) the counter-rotation of the arms holding forceps, connected through the gears (66) and (67) and the four bar links (68) and (69) to frames of the arms (70 and 71). About this it can be noted, however, that it is also possible to renounce to the further multiplication the gear (59) as it may suffice even the mere inversion of the commands, in the sense that, by imposing the same rotations both to the lower arm and to the upper gear which controls the inclination of the forceps towards the interior, the desired effect is achieved, simply in the first case with the arms open to 45° (90° of relative angle) the forceps are diametrically opposed, without multiplies instead in the same position opening the forceps present a relative angle of 90°. FIG. 9 presents precisely this comparison, in which the red four bar link controls the movement of the main arms (also red), the green commands the green gears, which in turn drive the support arms of the forceps, with two blue four bar links. Note also that in this configuration the teeth belonging to the arms in red, and those of the wheels in green are superimposed, but obviously work on different planes, just as they work on different planes the rods of the four bar links that in this view overlap.

Figure 10:
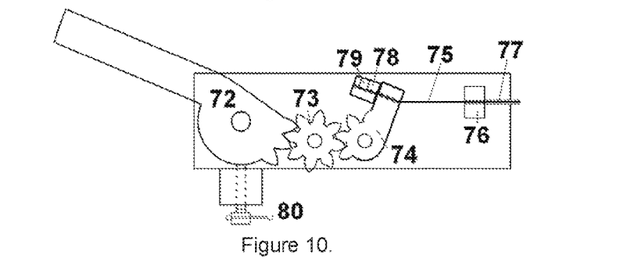
Figure 11:
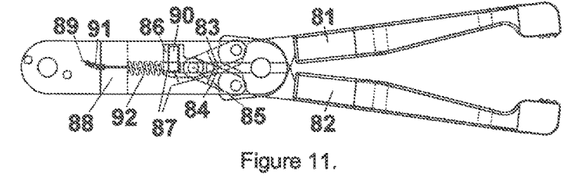

Finally, as regards the forceps, operable independently by rings (51) and (53), they are each controlled via cable which can slide within a tube of fixed length, (for example a section of a guide catheter) locked on both sides (both in the command and in the actuation areas) while the cable itself is held in tension by the same command ring that holds the forceps in normally closed position, and opens only if the operator raises the corresponding ring. FIG. 10 shows the interior of the area commanding opening and closing of the forceps, in which we notice the presence of the command bar (72), similar to (58) of FIG. 8, which, through the wheel (73), also similar to (57), controls the rotation of (74), connected to the cable (75), which is connected at the other end to the closing command of forceps. The fixed support of the instrument (76), must be connected to the cable incompressible guide (77), in case of its presence. Again with reference to the Figures, we note how a pawl (78) is used, together with a small allen (79), to lock the cable. And finally also note as the round shape of member (72) is actually a spiral descending from right to left, so that the screw (80) can lock the forceps after it has grasped the tissue, preventing the retrograde motion. Passing to the other side of the cable's incompressible guide, we note in FIG. 11 that the forceps is controlled by a tiny four bar link symmetrical composed of the prongs of the forceps (81) and (82) and by two arms (83) and (84), hinged between both of them (85) and to the rod (86) and the prongs of the forceps. The pin (85) is then constrained to slide in a special housing (87) that binds it to the centerline of the frame (88), while the rod (86) is connected to the other end of the control cable (89), which is fixed by means of an Allen screw (90), wire that protrudes from a hole of the same frame, which locks the other end of the guide of incompressible transmission (91) while a small spring (92) placed between the frame and the rod, when the cable is no longer under tension, thanks to the action of the operator, produces the symmetrical opening of forceps. Obviously such a subframe can be either fixed but rotated to any position relative to the arms retractors, which could also be rotatable around the axis of the frame itself, by rotating the guide together with its transmission cable.

Figure 12:
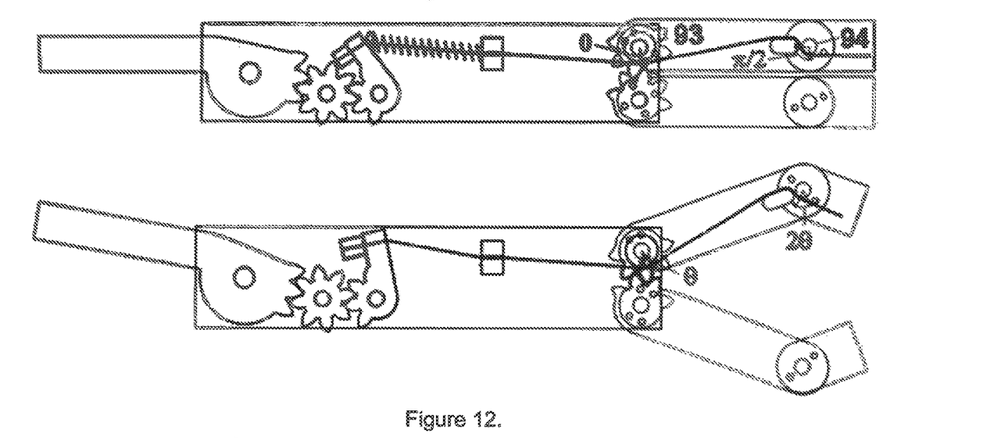

Alternatively one can study a solution for which, by introducing special pivot points, the length of the cable can still remain unaltered even when the arms can vary their degree of opening. In particular, FIG. 12 shows how this can be achieved, in a shortened edition, by comparison, as can be realized a constant length path. As can be seen in fact passing from the pivot between the central body and the first arm, the cable remains always tangent to the pin (93) of radius 2R, being then forced to turn by $\pi/2$ about a pivot of radius R (94) before going to control the forceps on the auxiliary arm. Instead, when the arm is tilted, the cable should stretch of $\theta \times 2R$, while correspondingly shortens of $2\theta \times R$ in the transition between the main and auxiliary arm, remaining the length constant.

Figure 13:
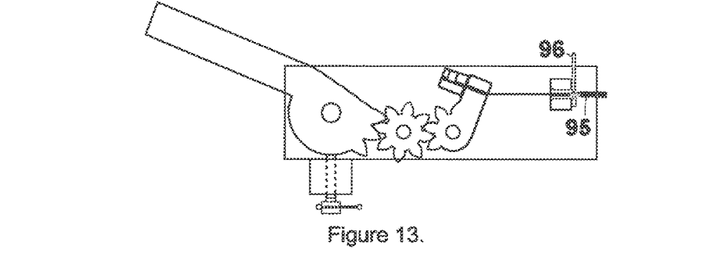
Figure 14:
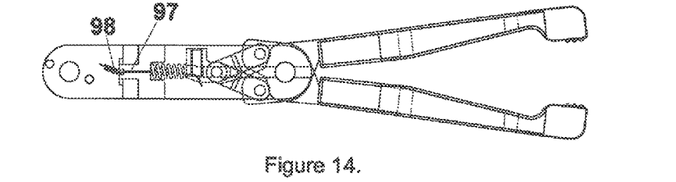

Returning to the possibility to rotate the forceps about its axis, this is illustrated in FIG. 13, obviously adding two additional rotating commands to the retractor instrument. In particular, we note in FIG. 13 as this is absolutely similar to FIG. 11, except for the presence, in this case mandatory, the transmission guide (95) which is fixed to a finger (96) used to rotate (the maximum of 180°) the guide itself and consequently the forceps. Obviously also the arm holding forceps must be modified, as shown in FIG. 14, in which we can see how the arm can rotate on a coaxial pin (97), whose rotation is controlled by the rotation of the guide (98), which must have a certain torsional stiffness, while the rest of the system remains unchanged.

Figure 15:
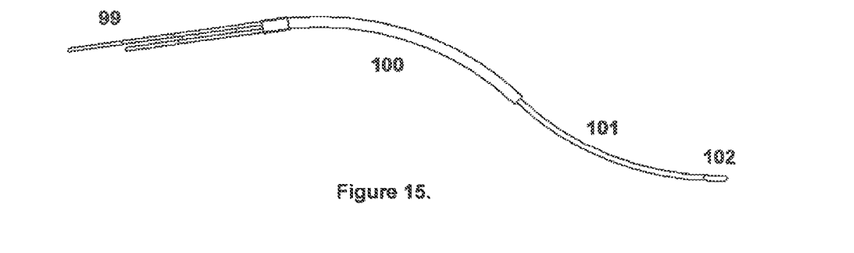

It should also be noted that by slightly modifying the gears or using cables and pulleys, it is possible to realize a clamp with a double curvature, such as that shown in FIG. 15, in which said double curvature occurs in the plane orthogonal to that of opening of the arms, with the rings command that can be curved or not (99) the body curved in a direction (100) and arms (101) and forceps (102) in the opposite direction which may simplify some operations.

As a further option, the two arms may also be composed of a multi-segmented system that would allow to vary the curvature of the single arm or of the two arms together, while maintaining the forceps aligned with the last element of the arm in the direction of curvature, while continue to bend in the opposite direction to the opening of the arms in the other plane. Of course it would be necessary to add on the body one or two additional rotating commands, which would work precisely to control the curvature. While in side view such an instrument could be totally similar to the previous one, it differs only for the presence of any one or two casters (103), and for the covering of the arms, made of flexible material.

Vice versa we note how inside the single element of the pluri-segmented arm should take the form shown in side view and section, where can be seen the pivot pin male (104) and female (105) at its ends, which allow precisely the rotation of a segment relative to the next, and the five command wires, central for the forceps (106), and lateral on the flat side (107) to allow counterrotation of forceps, while also maintaining the assembly, and lateral on the half-wedge side (108) for the control of the curvature of the arm. In this case the transmission of the counter rotation of the forceps would be a pulley or a four bar link with flexible connecting rods.

Figure 16:
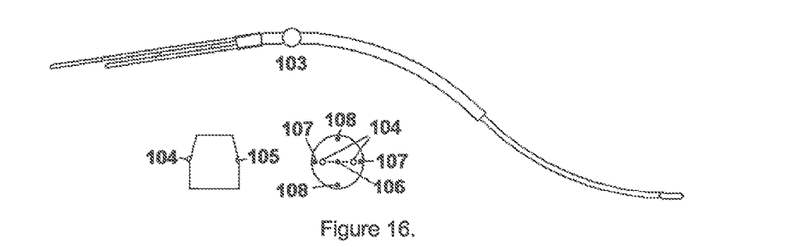
Figure 17:
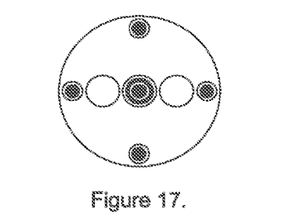

It would also be possible to realize both versions of the system with a double curvature, or flexible, in which the opening plane of the forceps with respect to the instrument itself is variable, and this is feasible by using a guide for the command of forceps capable of transmitting also torque, so that, using the command of FIG. 13, and the chassis of the forceps of FIG. 14, this can be achieved precisely as desired, for example, simply by passing the guide inside of the rigid curved arms, or enlarging the central hole in the multi segmented system of FIG. 16 so as to allow rotation of the guide with respect to the various segments of the flexible arms. FIG. 17 provides precisely the graphical representation of a segment seen in cross section in this case, where we note the central hole larger, containing cable and guide of transmission, the four peripheral wires and the two cups which act as a pivot at the sides.

Figure 18:
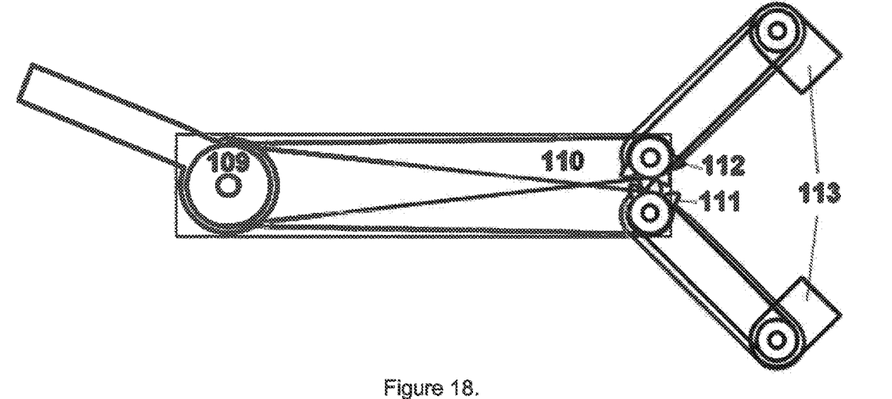
Figure 19:
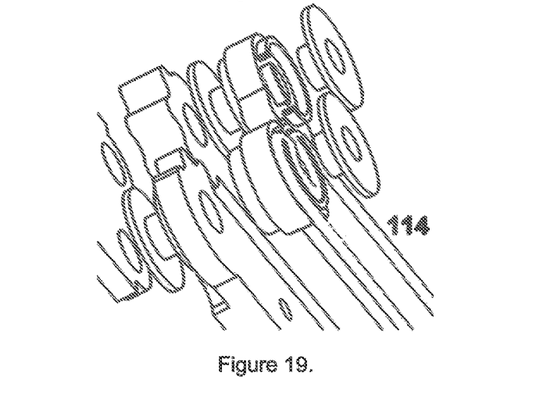

Starting then from the observation that it is not necessary to provide further amplification of the input command of the counter rotation of the forceps, as clarified in the second patent presented, CS2012A000032, since the rotation is relative to the central body and not to the arms, for which the angle between said arms and the forceps is however double of that imposed to the arms, we observe in FIG. 18 a simplified mechanism that realizes the intended movements, by deleting all except the internal gears which couple the opposite motion of the arms and of the arms holding forceps, by adopting a sort of transmission pulleys. In particular on the sides of the drum connected to the ring control (109) are placed two pulleys with a diameter double of that at the other end of the internal base (110), so as to achieve precisely the required movement amplification. Furthermore, while the pulley placed on one side commands the pulley which drives the opening of an arm (111), connected via gear to the counter-rotating arm, the other commands a different pulley (112), also copied with gears to a second counter-rotating pulley, so as to transmit rotations to the arms holding the forceps (113), always through a pair of pulleys, which transmit motion to both arms. In order to understand as the pulleys are made, given the sensitivity of the applications, may not allow undesired sliding, we observe in FIG. 19, as these pulleys anti slip can be built. In particular, the figure shows the path followed by the cable (114), which is blocked between the base and a cover, forcing it to a series of bends at a right angles, which prevent sliding.

Figure 20:
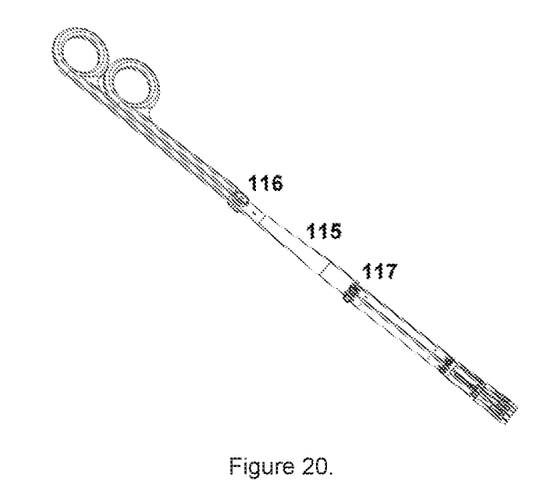

Turning to FIG. 20, we note that not necessarily the plane of rotation of the rings of command should coincide with that of the arms opening, and in fact is enough that the inner base (115), instead of being flat, has a twist of 90° between the zone of pivoting of the rings (116) and that of the base of the arms holding forceps (117), allowing precisely opening on a plane different from that of actuation.

Figure 21:
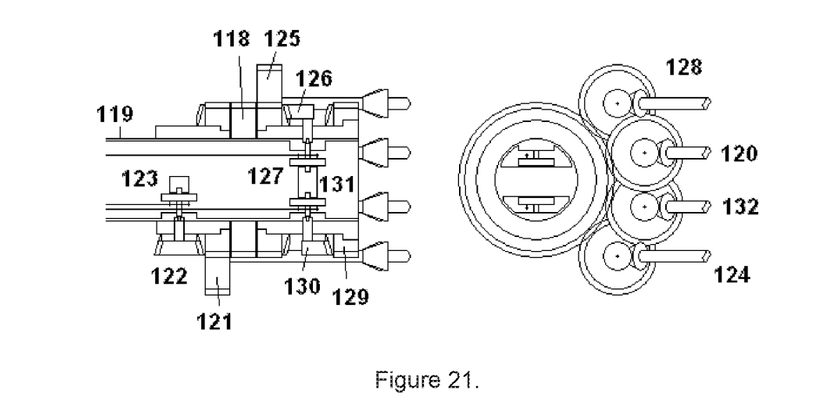

Finally it will be possible to develop forceps with two arms also controllable by robots, using a control scheme such as that shown by the patent application CS2010A000006, fully compatible with the present mechanics. The FIG. 21 shows how they can be made commands adapted to transmit the motion to these clamps through a series of motors and a combination of spur and bevel gears placed on the body of the instrument, replacing the rings. In particular, it is known as a spur gear (118), integral with the body of the instrument (119) is actuated by an external gear visible only in plan, controlled by means of a gear transmission (120) connected to a motor, not shown in the figure. And yet the gear (121), which engages through its conical portion with gear (122), controls the rocker arm (123) connected to the four bar link which then controls the mechanics of the gripper, the whole thing being controlled by the transmission (124). Obviously instead of the four bar link may be inserted a pair of bevel gears for controlling something that requires a rotation of more than 90°, the maximum attainable with all tranquility by a four bar link, such as the rotation of a forceps. Obviously, the one shown is only an example of rotation control+three individual commands, but may be realized in a similar way also commands of five or more actuators, replacing the rocker arms with cables and pulleys, or even to use hydraulic or pneumatic actuators. Returning to our Figures, the gears (125) engages again with the portion of the bevel gear (126), which controls the rocker arm (127) of the four bar link limited stroke, being the whole thing moved by the transmission (128), and similarly for the sequence (129), (130), (131) and (132).

Note that when you must rotate the clamp around its own axis, must simultaneously operate all motors at the same speed, while the single motor can implement the respective mechanisms in absence of rotation of the instrument.

In conclusion, what is presented here is an instrument with two arms bound by a common base, with a single control that lets you open the two arms while turning inward forceps with a single command and maintaining the open state or closure of the forceps themselves, while actuating the two remaining rings is achieved the opening and closing of the two forceps. In fact the internal mechanics can be varied at will, what matters is that there is a single gripper capable of opening two arms holding different instruments, which in the opinion of the authors of this patent should only be forceps, but could also be dissectors, needle holder, scissors, etc. The reason why we do not recommend this solution is that, while grabbing a body element from two sides and hold it or move it so as to facilitate the work with an independent second instrument, it makes sense, does not seem as logical to move one end of the instrument while holding the other. Anyway, such an embodiment would not present an element of innovation, being already provided herein.

Even the double rotation of the forceps with respect to the instrument can be further increased simply by altering the diameters of the pulleys or primitives of the gears, or by adding additional pulleys or overdrive gears in the transmission path.

The invention claimed is:

1. An apparatus for single access laparoscopy the apparatus comprising:
   a main body having a tubular shape including a plurality of fins disposed thereon;
   a first moving member inside the main body, the first moving member defining a first-moving-member axis, the first moving member being configured to move about the first-moving-member axis, the first moving member including a pulley;
   a first arm, the first arm being coupled to the first moving member;
   a first forceps, the first forceps being coupled to the first arm;
   a second arm, the second arm being coupled to the first moving member;
   a second forceps, the second forceps being coupled to the second arm;
   a first mechanical control coupled to the first moving member, such that a single movement of the first mechanical control moves both the first and second arms; and
   second and third mechanical controls enabling independent opening of the first and second forceps, the second and third controls being lockable upon request individually, the second and third mechanical controls can be blocked by the fins.

2. An apparatus for single access laparoscopy, the apparatus comprising:
   a main body having a tubular shape;

a first moving member inside the main body, the first moving member defining a first-moving-member axis, the first moving member being configured to move about the first-moving-member axis;

a first arm, the first arm being coupled to the first moving member;

a second moving member inside the main body, the second moving member defining a second-moving-member axis, the second moving member being configured to move about the second moving-member axis wherein the first arm is coupled to the first moving member via the second moving member, the second moving member including a pulley, wherein the first arm is coupled to the first moving member via the second moving member;

a first forceps, the first forceps being coupled to the first arm;

a second arm, the second arm being coupled to the first moving member;

a second forceps, the second forceps being coupled to the second arm;

a first mechanical control coupled to the first moving member, such that a single movement of the first mechanical control moves both the first and second arms; and second and third mechanical controls enabling independent opening of the first and second forceps, the second and third controls being lockable upon request individually.

3. An apparatus for single access laparoscopy, the apparatus comprising:

a main body having a tubular shape;

a first moving member inside the main body, the first moving member defining a first-moving-member axis, the first moving member being configured to move about the first-moving-member axis, the first moving member including a pulley;

a first arm, the first arm being coupled to the first moving member;

a first forceps, the first forceps being coupled to the first arm;

a second arm, the second arm being coupled to the first moving member;

a second forceps, the second forceps being coupled to the second arm;

a first mechanical control coupled to the first moving member, such that a single movement of the first mechanical control moves both the first and second arms; and second and third mechanical controls enabling independent opening of the first and second forceps.

* * * * *